United States Patent [19]

Lu-Dai Sung et al.

[11] Patent Number: 5,322,528
[45] Date of Patent: Jun. 21, 1994

[54] COMPOSITION OF MATTER FOR HIGH TEMPERATURE PHENOLPHTHALEIN-, PHENOLPHMALIDE-, FLUORENE-, XANTHANE-, AND ANTHRONE-S-TRIAZINES THAT ARE SOLUBLE IN DIESEL FUEL

[75] Inventors: Rodney Lu-Dai Sung, Fishkill, N.Y.; Thomas F. DeRosa, Passaic, N.J.; Benjamin J. Kaufman, Hopewell Jct., N.Y.

[73] Assignee: Texaco Inc., White Plains, N.Y.

[21] Appl. No.: 860,798

[22] Filed: Mar. 30, 1992

[51] Int. Cl.$^5$ ............................................. C10L 1/22
[52] U.S. Cl. ........................................................ 44/336
[58] Field of Search ............................................ 44/336

[56] References Cited

U.S. PATENT DOCUMENTS

| | | | |
|---|---|---|---|
| 2,232,871 | 2/1941 | Schmidt et al. | 44/336 |
| 3,206,407 | 9/1965 | Lutwack | 44/336 |
| 3,245,992 | 4/1966 | Dexter et al. | 44/336 |

*Primary Examiner*—Jerry D. Johnson
*Attorney, Agent, or Firm*—George J. Darsa; Kenneth R. Priem; Christopher Nicastri

[57] ABSTRACT

A composition of matter comprising a mixture of:
a) phenolphthaleins-s-triazines;
b) phenolphthalides-s-triazines;
c) 9,9-bis-(4-hydroxy phenyl)fluorene -triazines;
d) 3,6-dihydroxyspiro[fluorene-9,9-xanthane]-s-triazines;
e) 10,10-bis-(4-hydroxyl phenyl)anthrone-s-triazines; and
f) 9,9,10,10-tetrakis-(4-hydroxylphenyl)-anthracene-s-triazines.

2 Claims, No Drawings

COMPOSITION OF MATTER FOR HIGH TEMPERATURE PHENOLPHTHALEIN-, PHENOLPHMALIDE-, FLUORENE-, XANTHANE-, AND ANTHRONE-S-TRIAZINES THAT ARE SOLUBLE IN DIESEL FUEL

BACKGROUND OF THE INVENTION

This invention relates to a chemical method of decreasing nitric oxide, NOx, levels, and more particularly to a composition of matter for reducing $NO_x$ levels in diesel fuels.

Nitrogen oxides are the oxidation products of elemental nitrogen, organic, or inorganic nitrogen and oxygen at elevated temperatures. Nitrogen oxides include nitric oxide, NO; nitrogen dioxide, $NO_2$; nitrogen trioxide, $NO_3$; dinitrogen trioxide, $N_2O_3$; tetranitrogen pentaoxide, $N_4O_5$; tetranitrogen hexaoxide, $N_4O_6$; nitrous oxide, $N_2O$; and the like. Elevated temperatures required to prepare these oxidation products are routinely obtained in internal combustion engines utilizing gasoline, diesel, or aviation fuel.

There are very strong ecological and environmental reasons to reduce or ideally eliminate NOx as an internal combustion oxidation product. Once produced, NOx is directly responsible for acid rain and photochemical smog. Moreover, chronic exposure to NOx has been directly linked with restricted pulmonary compliance in non-smoking healthy males; acute respiratory disease among children living in "high exposure" towns in Czechoslovakia; and a key irritant cited for the high incidence of chronic bronchitis among Japanese postal workers servicing urban centers as outlined in Medical and Biologic Effects of Environmental Pollutants by the National Academy of Sciences, 1977.

Numerous physical methods have been suggested to reduce or eliminate NOx. Certain proposed techniques involve a great deal of capital outlay and require major consumption of additives, scrubbers, etc. For example, U.S. Pat. No. 3,894,141 proposes a reaction with liquid hydrocarbons; U.S. Pat. No. 4,405,587 proposes high temperature burning with a hydrocarbon; U.S. Pat. No. 4,448,899 proposes reacting with an iron chelate; U.S. Pat. No. 3,262,751 reacts NOx with a conjugated diolefin. U.S. Pat. No. 3,900,554 utilizes a combination of ammonia and oxygen to react with nitric oxide.

Application of these reactions discussed above imposes organic pollutant disposal problems along with the attendant problems of toxicity and malodorous environments. In addition, they require the presence of oxygen and are relatively expensive. And, all of these methods discussed must deal with the problem of the odor of ammonia and its disposal. Moreover, these methods also suffer from the drawback of requiring controlled environments which make them impossible to use in mobile vehicles.

Thus, an object of the present invention is to provide an economical means and/or a composition of matter that effectively reduces $NO_x$ in diesel fuels.

DISCLOSURE STATEMENT

U.S. Pat. No. 4,731,231 discloses a method of reducing NOx levels for stationary sources of NOx. such as power plants utilizing fossil fuel to generate power. However, this invention is limited to stationary $NO_x$ sources only. This invention is not applicable to dynamic or non-stationary $NO_x$ sources, for example, gasoline or diesel powered vehicles, which means that a method for $NO_x$ reduction was not achieved.

Japanese Publication No. J55051-420 utilizes halocyanuric acid to remove malodorous fumes, e.g., mercaptans, sulfides, disulfides, ammonia or amines from gases by contact therewith followed by contact with activated carbon. Temperatures are reported in this publication as less than 80° C.; and classical acid/base interactions appear to be involved (not pyrolysis decomposition products of the halocyanuric acid).

Back et al., Can. J. Chem. 46.531(1968), discloses the effect of nitric oxide on the photolysis of isocyanic acid, HNCO, the decomposition product of cyanuric acid. An increase of nitrogen concentration in the presence of large amounts of nitric oxide was observed when nitric oxide came in contact with isocyanic acid or the photolysis product of HNCO. The increased concentration of nitrogen was attributed by the authors directly to nitric oxide reduction.

Furthermore, use of cyanuric acid as a source of isocyanic acid (HNCO) is well known in the art. See, for example, Okable, J. Chem. Phys., 53, 3507 (1970) and Perry, J. Chem. Phys. 82,5485 (1985). However, it was never suggested that cyanuric acid could be useful in the removal of nitric oxides from non-stationary sources because of inherent problems in the use of cyanuric acid.

SUMMARY OF THE INVENTION

The present invention provides a composition of matter comprising a mixture of:
a) mono(phenolphthalein ether)-di-hydroxy-triazine;
b) [o-(Phenolphthalein)-o'-(phenolphthalein)-]-diether-hydroxyl-s-triazine;
c) phenolphthalein-di-(di-hydroxy-s-triazine)ether;
d) poly[phenolphthalein-co-(hydroxyl)s-triazine]ether;
e) poly[star(phenolphthalein-co-s-triazine)ether];
f) mono(phenolphthalide ether -di-hydroxy-s-triazine);
g) [o-[phenolphthalide)-o'-(phenolphthalide)-[diether-hydroxyl-s-triazine;
h) phenolphthalide-di-(di-hydroxyl-s-triazine)-ether;
i) poly[phenolphthalide-co-(hydroxyl)-s-triazine]ether;
j) poly[star (phenolphthalide -co-s-triazine)-ether];
k) 9-(4-hydroxylphenyl)-9-(4-[di-hydroxyl-s-triazine] phenylether)fluorene;
l) 4-(o-phenyl fluorene)-4-(o'-phenyl fluorene) diether hydroxyl-s-triazine;
m) di-9-[4(di-hydroxyl-s-triazine) phenyl ether] fluorene;
n) poly(9,9-phenylfluorene)-co-[(hydroxyl)-s-triazine]-ether;
o) poly[star (9,9-phenyl fluorene)-co-(s-triazine) -ether];
p) 3-hydroxy-6-(di-hydroxy-s-triazine)spiro(fluorene-9,9-xanthane);
q) 3,6-di(di-hydroxy-s-triazine)spiro(fluorene-9,9-xanthane);
r) poly[3,6-dihydroxylspiro(fluorene-9,9-xanthane)-co-(hydroxyl)-s-triazine] ether;
s) poly[star [tri (3,6-dihydroxyl(spiro [fluorene-9,9 xanthane -co-s-triazine] -ether];
t) 10,10-(4-hydroxyl phenyl)-dihydroxyl-s-triazine ether)-anthrone;
u) 10,10-[4-(o)-4'(o')-diether-s-triazine] anthrone;
v) 10,10-bis-(4-di-hydroxyl-s-triazine)ether-anthrone;
w) poly[10,10-(4-oxyphenyl)-4'(hydroxyl-s-triazine)anthrone];
x) poly[star (tri-[10,10'-dihydroxylphenyl-anthrone)-co-(s-triazine)-ether];

y) 9,10,10-tri(4-hydroxyl phenyl)-10-[4-(di-hydroxyl-s-triazine) phenyl ether] anthracene;
aa) 9,9 [4-(o,o'-hydroxyl-s-triazine)-phenyl ether]-10,10-bis (4-hydroxylphenyl)-anthracene;
bb) 9,9-bis [4-(dihydroxyl-s-triazine)-phenyl ether]-10,10-bis-(4-hydroxyl phenyl) - anthracene;
cc) 9-(4-hydroxyl phenyl)-10-(4-hydroxyl phenyl) -9-[(4-dihydroxyl-s-triazine) phenyl ether] -10-[4-dihydroxyl-s-triazine)-phenyl ether]-anthracene;
dd) 9,9,-[(4-o,o',-hydroxyl-s-triazine-phenyl ether) -10,10-(4-o,o'-hydroxyl s-triazine)-phenyl ether]-anthracene;
ee) 9,9,10,10-tetrakis [(4-dihydroxyl-s-triazine)-phenyl ether] - anthracene;
ff) 9,9-[4-poly(oxyphenyl-co-4-hydroxyl-s-triazine)-phenyl) -ether)]-10,10-bis (4-hydroxyl phenyl) anthracene;
gg) 9,9-[4-poly(oxyphenyl-co-4-hydroxyl-s-triazine) phenyl ether)]-10-(4-hydroxyl phenyl)-10-(4-(dihydroxyl-s-triazine-o-phenylether) anthracene;
hh) 9,9-[4-poly(oxyphenyl-co-4-hydroxyl-s-triazine) phenyl ether)]-10,10-bis(4-(dihydroxyl-s-triazine) phenyl ether)-anthracene;
ii) 9,10-[4-poly(oxyphenyl-co-4-hydroxyl-s-triazine) phenyl ether)]-9,10-bis-(4-hydroxyl phenyl)-anthracene;
jj) 9,10-[4-poly(oxyphenyl-co-4-hydroxyl-s-triazine) phenyl ether)]-9-(4-hydroxyl phenyl)-10 - (4-dihydroxyl-s-
triazine) -phenyl ether-anthracene; and
kk) 9,10-[4-poly (oxyphenyl-co-4-hydroxyl-s-triazine) phenyl ether]-9,10-bis-(4-dihydroxyl-s-triazine-phenyl ether)-anthracene.

DETAILED DESCRIPTION OF THE INVENTION

The composition of matter of the present invention includes mono, di- and triethers of cyanuric acid. These ethers, i.e., s-triazines, are categorized in various types (i.e., Type I, Type II, etc.) of which each type (i.e., group of s-triazines) is prepared as set forth below to produce these s-triazines as listed above in the Summary of the Invention, described and listed below in Type I.

Type I—Phenolphthalein -s-triazines

A compositon of matter is prepared by the process comprising reacting phenolphthaleins represented by the formula

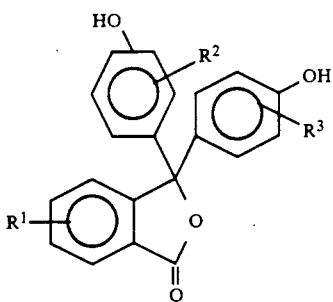

where $R^1$, $R^2$, and $R^3$ are each a ($C_1$–$C_{10}$) linear, cyclic, branched or aromatic hydrocarbon,
with cyanuric chloride, thereby preparing said composition of matter which comprises:
a) mono(phenolphthalein ether)-di-hydroxy-triazine;
b) [o-(Phenolphthalein)-o'-(phenolphthalein)-]-diether-hydroxyl-s-triazine;
c) phenolphthalein-di-(di-hydroxy-s-triazine)ether;
d) poly[phenolphthalein-co-(hydroxyl)s-triazine]ether; and
e) poly[star(phenolphthalein-co-s-triazine)ether].

Type II—Phenolphthalein -s-triazines

A composition of matter is prepared by the process comprising reacting phenolphthalides represented by the formula

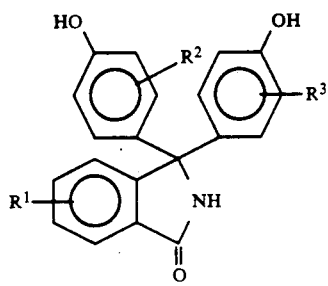

where $R^1$, $R^2$, and $R^3$ are each a ($C_1$–$C_{10}$) linear, cyclic, branched or aromatic hydrocarbon,
with cyanuric chloride, thereby preparing said composition of matter which comprises:
f) mono(phenolphthalide ether -di-hydroxy-s-triazine);
g) [o-[phenolphthalide)-o'-(phenolphthalide)-[diether-hydroxyl-s-triazine;
h) phenolphthalide-di-(di-hydroxyl-s-triazine)-ether;
i) poly[phenolphthalide-co-(hydroxyl)-s-triazine]ether; and
j) poly[star (phenolphthalide -co-s-triazine)-ether].

Type III—9,9-bis (4-hydroxylphenyl) fluorene -s-triazines

A composition of matter is prepared by the process comprising reacting 9,9-bis (4-hydroxylphenyl) fluorenes represented by the formula

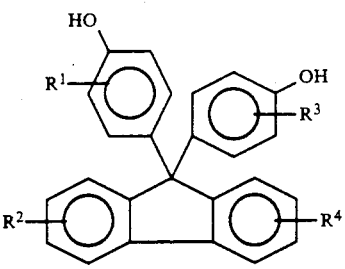

where $R^1$, $R^2$, and $R^3$ and $R^4$ are each a ($C_1$–$C_{10}$) linear, cyclic, branched or aromatic hydrocarbon,
with cyanuric chloride, thereby preparing said compositon of matter which comprises:
k) 9-(4-hydroxylphenyl)-9-(4-[di-hydroxyl-s-triazine] phenylether)fluorene;
l) 4-(o-phenyl fluorene)-4-(o'-phenyl fluorene) diether hydroxyl-s-triazine;
m) di-9-[4(di-hydroxyl-s-triazine) phenyl ether] fluorene;
n) poly(9,9-phenylfluorene)-co-[(hydroxyl)-s-triazine]-ether; and
o) poly[star (9,9-phenyl fluorene)-co-(s-triazine) -ether];

Type IV—3,6-Dihydroxylspiro [Fluorene -9,9 Xanthane]-s-triazines

A composition of matter is prepared by the process comprising reacting 3,6-dihydroxylspiro [fluorene -9,9 xanthanes] represented by the formula

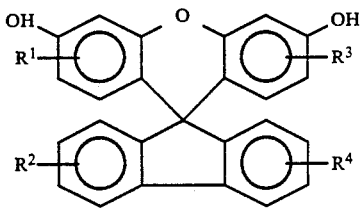

where $R^1$, $R^2$, $R^3$ and $R^4$ are each a ($C_1C_{10}$) linear, cyclic, branched or aromatic hydrocarbon, with cyanuric chloride, thereby preparing said composition of matter which comprises:
p) 3-hydroxy-6-(di-hydroxy-s-triazine)spiro(fluorene-9,9-xanthane);
q) 3,6-di(di-hydroxy-s-triazine)spiro(fluorene-9,9-xanthane);
r) poly[3,6-dihydroxylspiro(fluorene-9,9-xanthane)-co-(hydroxyl)-s-triazine]ether; and
s) poly[star [tri (3,6-dihydroxyl(spiro [fluorene-9,9 xanthane -co-s-triazine]-ether].

Type V—10,10-bis (4-Hydroxylphenyl) Anthrone -s-Triazines

A composition of matter is prepared by the process comprising reacting 10,10-bis(4-hydroxylphenyl) anthrones represented by the formula

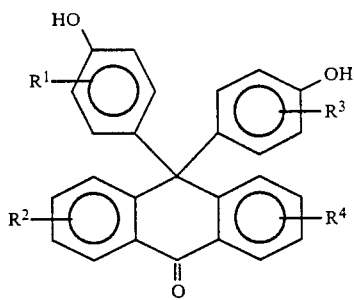

where $R^1$, $R^2$, $R^3$, $R^4$ and $R^5$ are each a ($C_1$-$C_{10}$) linear, cyclic, branched or aromatic hydrocarbon, with cyanuric chloride, therby preparing said composition of matter which comprises:
t) 10,10-(4-hydroxyl phenyl)-dihydroxyl-s-triazine ether)-anthrone;
u) 10,10-[4-(o)-4'(o')-diether-s-triazine] anthrone;
v) 10,10-bis-(4-di-hydroxyl-s-triazine)ether-anthrone;
w) poly[10,10-(4-oxyphenyl)-4'(hydroxyl-s-triazine)anthrone]; and
x) poly[star (tri-[10,10'-dihydroxylphenyl-anthrone)-co-(s-triazine)-ether].

Type VI—9,9,10,10-Tetrakis (4-Hydroxylphenyl) Antracene-s-triazines

A composition of matter prepared by the process comprising reacting 9,9,10,10-tetrakis (4-hydroxylphenyl)-anthracenes represented by the formula

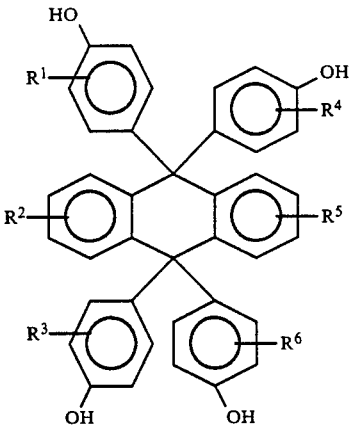

where $R^1$, $R^2$, $R^3$, $R^4$, $R^5$, and $R^6$ are each a ($C_1$-$C_{10}$) linear, cyclic, branched or aromatic hydrocarbon, with cyanuric chloride, thereby preparing said composition of matter which comprises:
y) 9,10,10-tri(4-hydroxyl phenyl)-10-[4-(di-hydroxyl-s-triazine) phenyl ether] anthracene;
aa) 9,9 [4-(o,o'-hydroxyl-s-triazine)-phenyl ether]-10,10-bis (4-hydroxylphenyl)-anthracene;
bb) 9,9-bis [4-(dihydroxyl-s-triazine)-phenyl ether]-10,10-bis-(4-hydroxyl phenyl) - anthracene;
cc) 9-(4-hydroxyl phenyl)-10-(4-hydroxyl phenyl) -9-[(4-dihydroxyl-s-triazine) phenyl ether]-10-[4-dihydroxyl-s-triazine)-phenyl ether]-anthracene;
dd) 9,9,-[(4-o,o',-hydroxyl-s-triazine-phenyl ether) -10,10-(4-o,o'-hydroxyl s-triazine)-phenyl ether]-anthracene;
ee) 9,9,10,10-tetrakis [(4-dihydroxyl-s-triazine)-phenyl ether]- anthracene;
ff) 9,9-[4-poly(oxyphenyl-co-4-(hydroxyl-s-triazine)-phenyl) -ether)]-10,10-bis (4-hydroxyl phenyl)-anthracene;
gg) 9,9-[4-poly(oxyphenyl-co-4-hydroxyl-s-triazine) phenyl ether)]-10-(4-hydroxyl phenyl)-10-(4-(dihydroxyl-s-triazine-o-phenylether) anthracene;
hh) 9,9-[4-poly(oxyphenyl-co-4-hydroxyl-s-triazine) phenyl ether)]-10,10-bis(4-(dihydroxyl-s-triazine) phenyl ether)-anthracene;
ii) 9,10-[4-poly(oxyphenyl-co-4-hydroxyl-s-triazine) phenyl ether)]-9,10-bis-(4-hydroxyl phenyl)-anthracene;
jj) 9,10-[4-poly(oxyphenyl-co-4-hydroxyl-s-triazine) phenyl ether)]-9-(4-hydroxyl phenyl)-10 - (4-dihydroxyl-s-triazine) -phenyl ether-anthracene; and
kk) 9,10-[4-poly (oxyphenyl-co-4-hydroxyl-s-triazine) phenyl ether]-9,10-bis-(4-dihydroxyl-s-triazine-phenyl ether)-anthracene.

The main areas to which the present invention is directed to are: (1) the known reducing strength of isocyanic acid, HNCO; (2) its preparation by thermally decomposing cyanuric acid, (HNCO)₃; (3) dissolution of cyanuric acid in diesel fuel; (4) dissolution of cyanuric acid or its derivatives that, upon thermal decomposition, generate the reducing agent, isocyanic acid, HNCO; and (5) thermally enhancing the crucial reducing agent precursor, cyanuric acid or its derivatives, to survive the internal engine combustion event.

The present composition of matter invention provides a mixture of materials addressing the aforementioned concerns. These materials may be categorized as thermally stable molecules designed to structurally mimic unburnt hydrocarbon and polynuclear aromatic hydrocarbons in diesel engine exhaust. The precursors of this invention differ from simple diesel exhaust in that all materials in their invention contain at least two phenolic groups. The explicit purposes for including at least two phenolic groups are listed below:

i) phenolics provide a copious supply of reactive protons upon thermal decomposition;
ii) incorporation of cyanuric acid will utilize phenolic reaction sites to generate the corresponding ether; and
iii) phenolics are easily modified to enhance diesel fuel solubility.

Each of the above will be separately expanded upon. A crucial chemical requirement of cyanuric acid or hydroxyl-s-triazine incorporation is that at least one, and preferably two, free hydroxyl groups must be present. The chemical underpinning from this requirement is that upon thermal unzipping free hydroxyl groups on s-triazine will generate the $NO_x$ reducing agent, isocyanic acid. Depicted below in Equations 1a, 1b, 1c, and 1d are four versions of hydroxyl-s-triazines undergoing thermal decomposition.

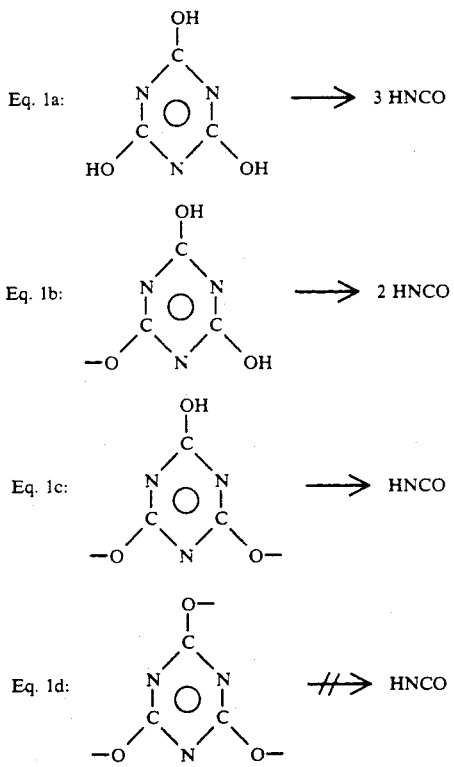

One or two covalent ether bonds are attached to the s-triazine phenolic portion of the single oligomeric backbone.

In these cases, however, where cyanuric acid has formed the corresponding tri-ether, unless a source of labile protons become available, thermal decomposition of the tri-ether will fail to generate isocyanuric acid. This invention also addresses a readily available source of labile protons.

A readily available source of protons to enable isocyanuric to be generated upon thermal decomposition of tri-ether-s-triazines are phenolics. Prior to an actual thermal decomposition, ortho-alkyl substituted phenolics routinely under 'ortho-quinone methide' while para-alkyl substituted phenolics under 'para-quinone methide' thermal rearrangements (Equations 2a and 2b, respectively).

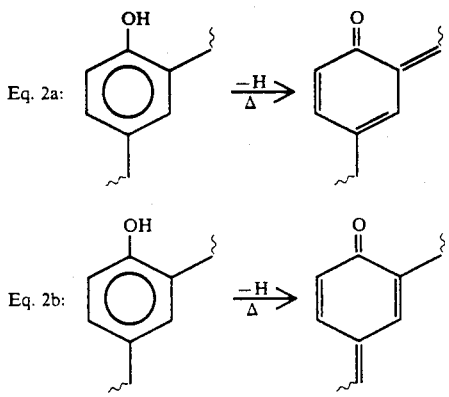

In both cases, acidic phenolic protons become available to augment the proton deficiency of triether-s-triazines to generate isocyanic acid, HNCO. During thermal degradation phenolic portion will undergo degradation before s-triazine ether. This thermally-induced chemical process will essentially transform it into a hydrogen atom source.

The incorporation of cyanuric acid into these thermally stable molecular well generate mono-, di-, and tri-ether-s-triazine, the ratio of which is contingent upon stoichiometric and experimental parameters.

By skillful manipulation of experimental parameters, however, one or more structural orientations may be favored at the expense of another. Structural permutations (i.e., components) of each class (i.e., type) which comprise the products making up the present compositon of matter are provided below, where "a" varies from 1 to 3000, and where the corresponding nomenclature is provided below the structures in Table I.

Type 1 - Phenolphthalein-s-triazines

-continued
a) 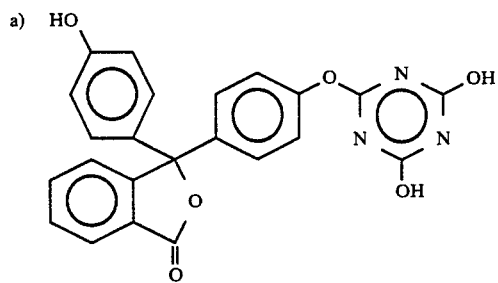
b) 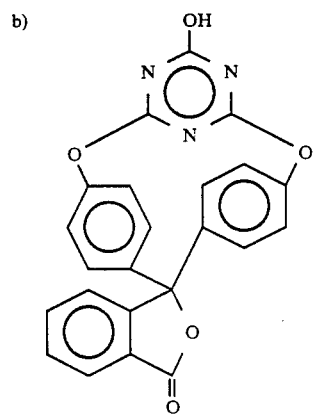
c) 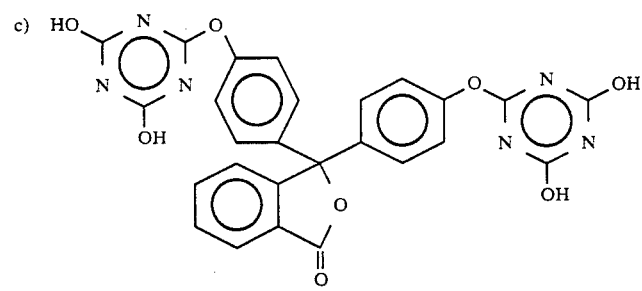
d) 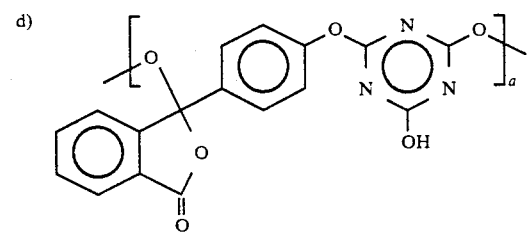
e) 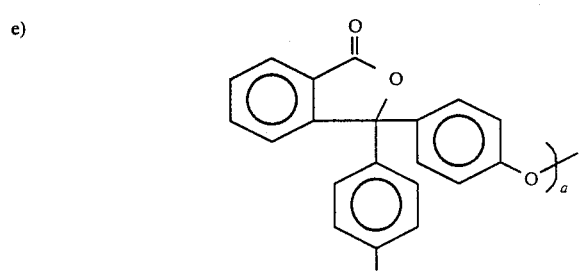

-continued
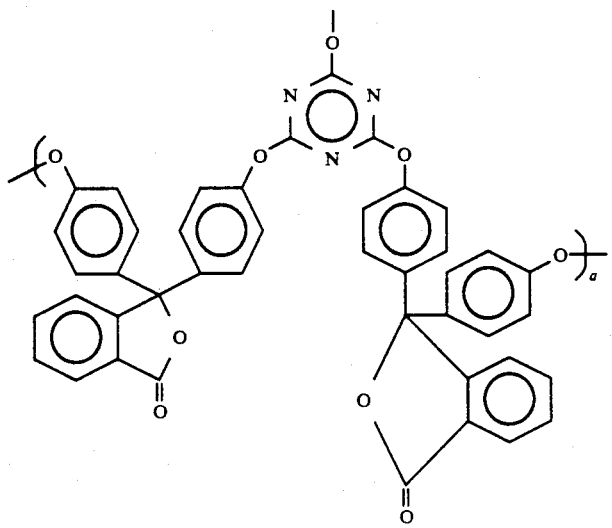
Type II - Phenolphthalide-s-triazines
f) 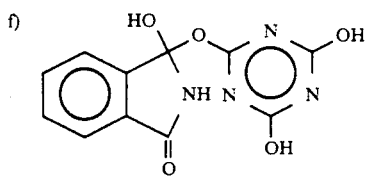
g) 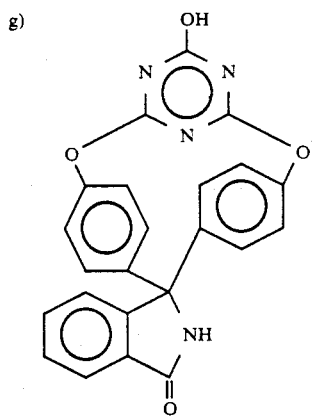
h) 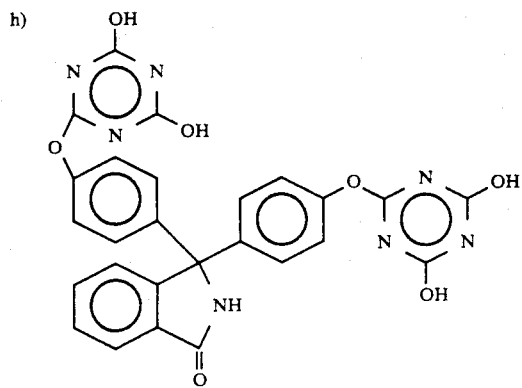

i) 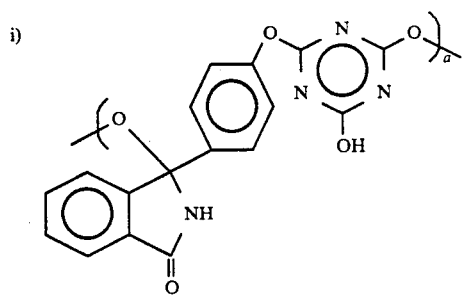
j) 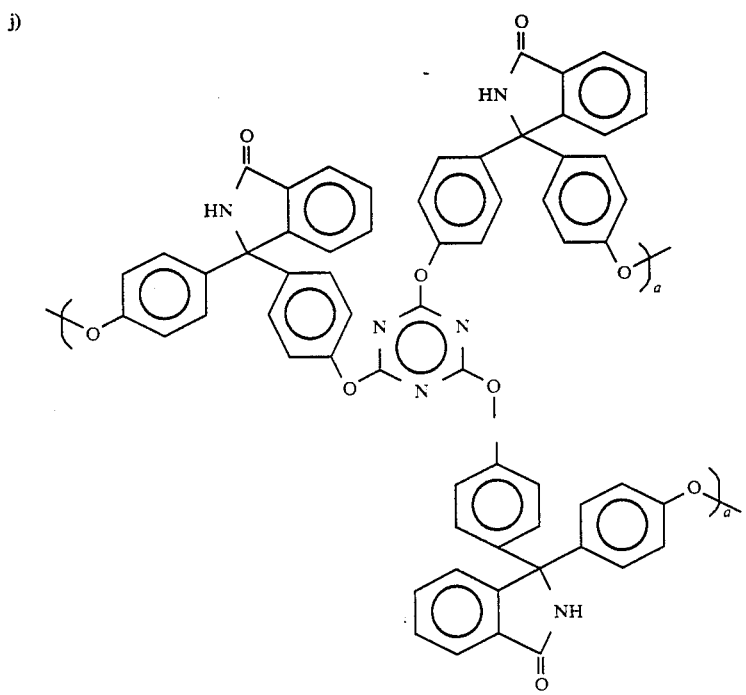
Type III - 9,9 Bis(4-hydroxylphenyl)fluorene-s-triazines
k) 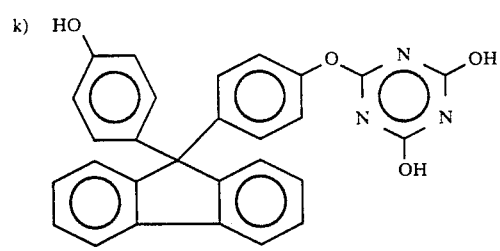
l) 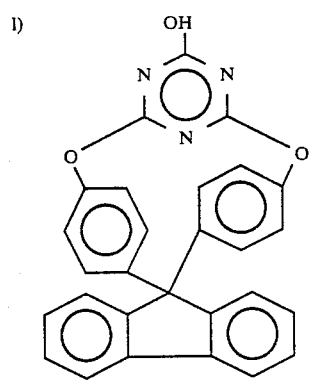

m) 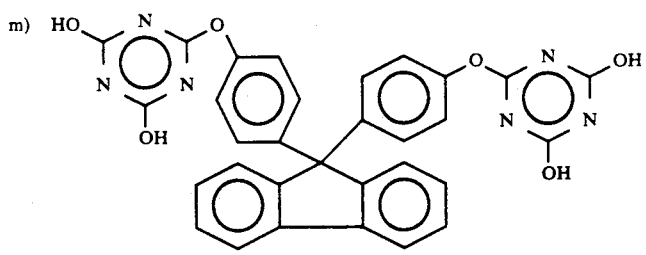
n) 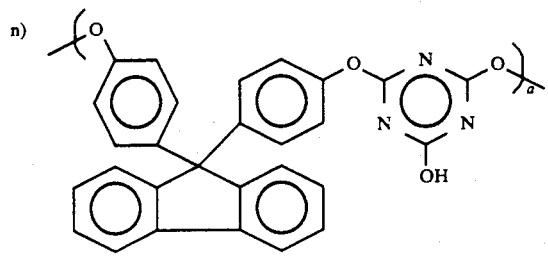
o) 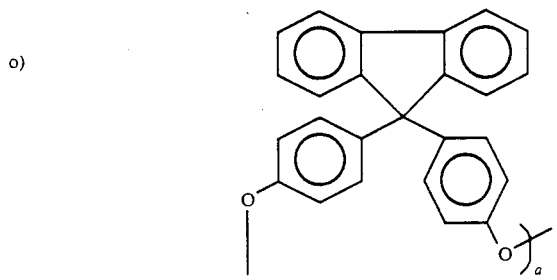
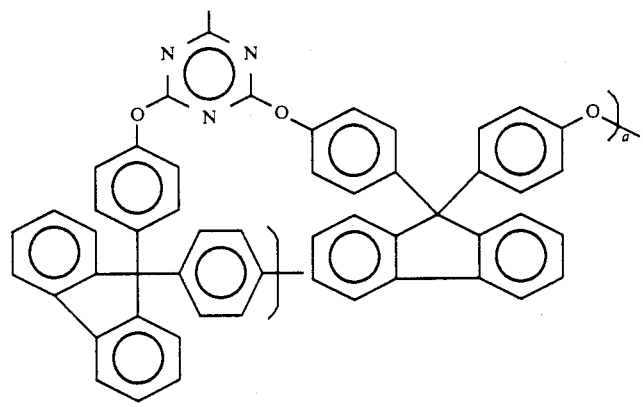
Type IV 3,6-dihydroxylspiro[fluorene-9,9 xanthane]-s-triazines
p) 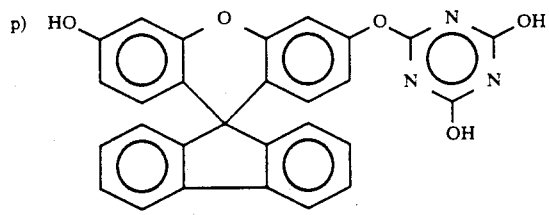
q) 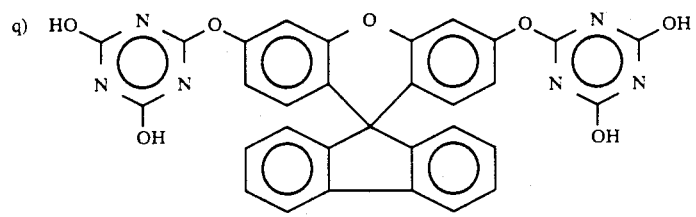

-continued
r) 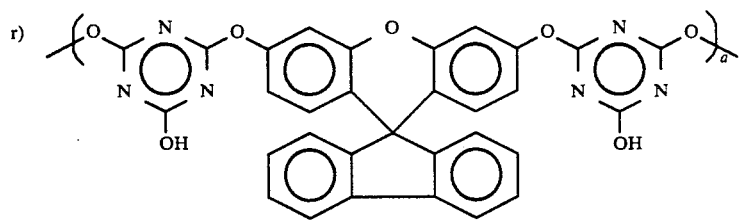
s) 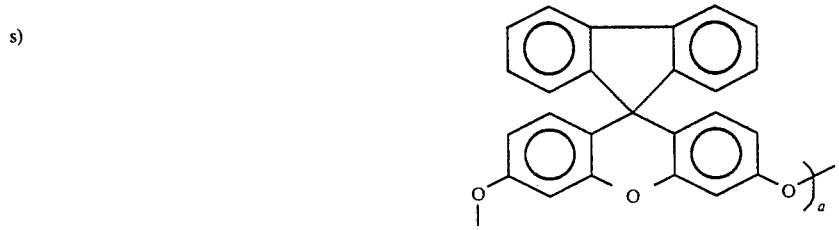
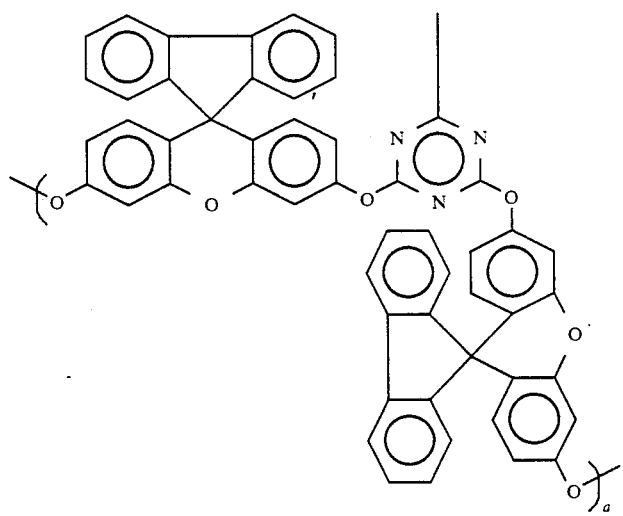
Type V 10,10-Bis(4-hydroxylphenyl)anthrone-s-triazines
t) 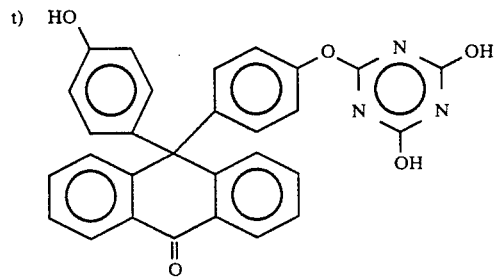

u) 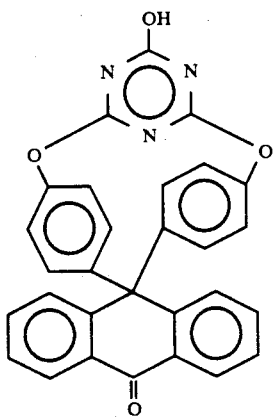
v) 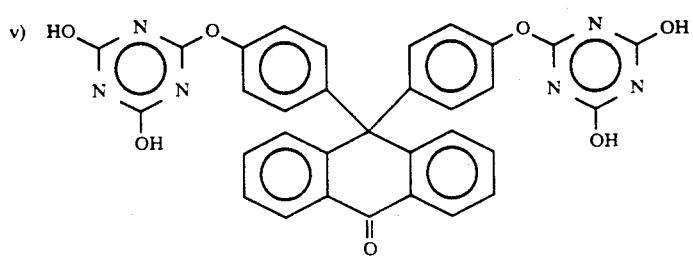
w) 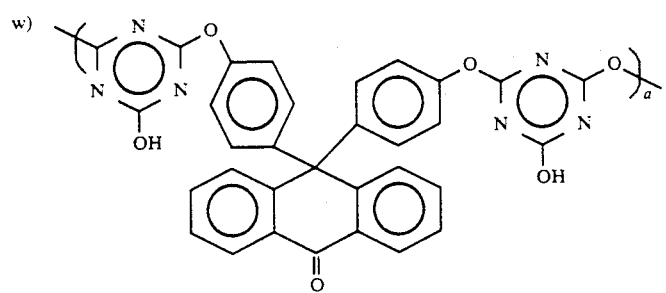
x) 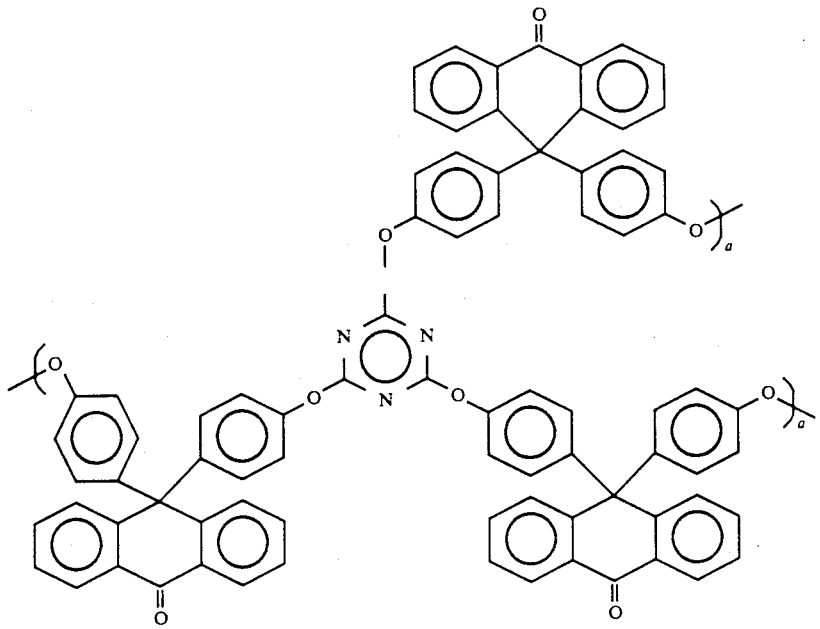
Type VI - 9,9,10,10-tetrakis(4-hydroxylphenyl)-anthracene-s-triazines.

y) 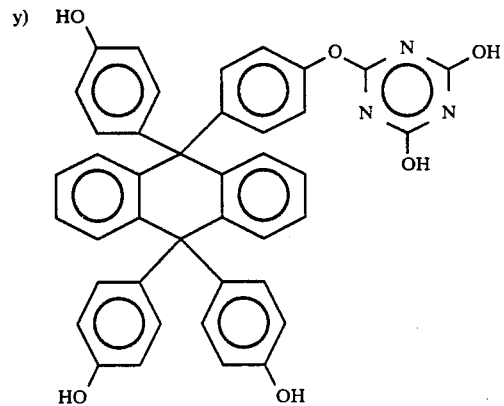
aa) 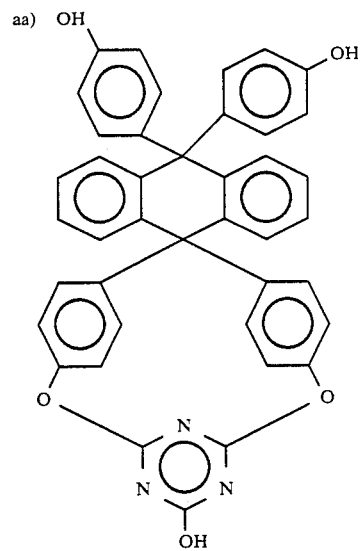
bb) 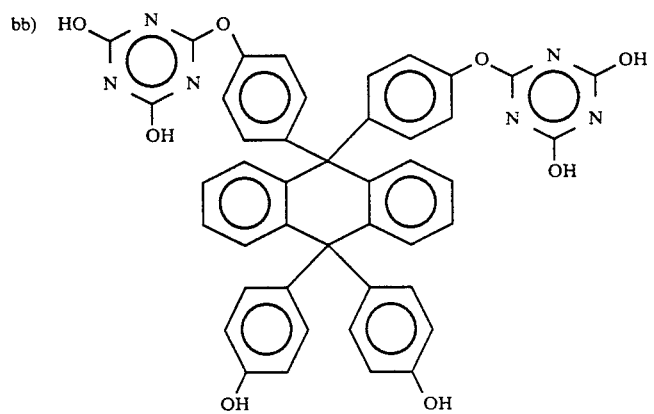

-continued
cc) 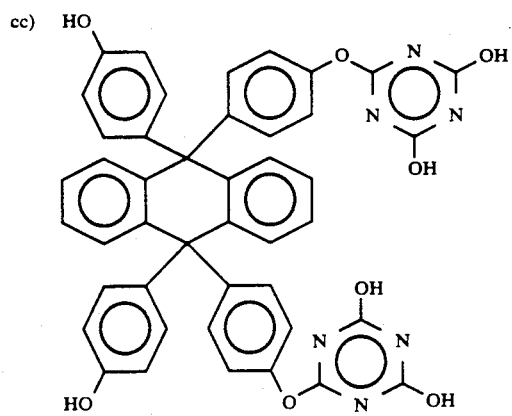
dd) 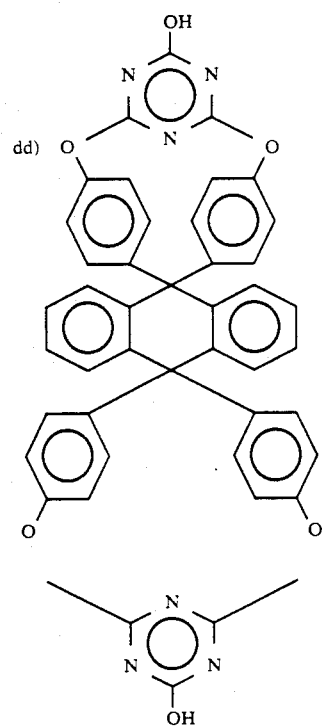
ee) 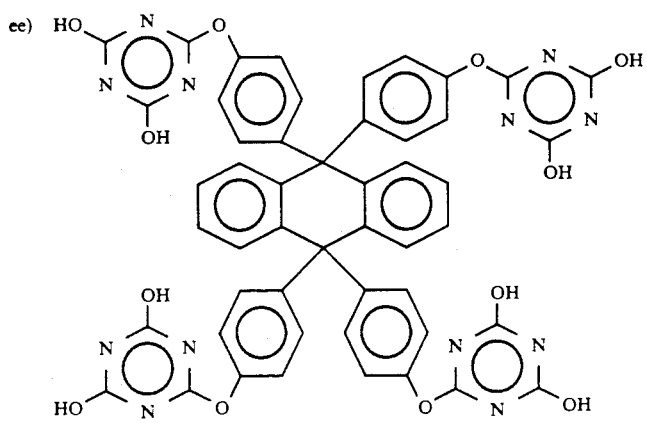

ff) 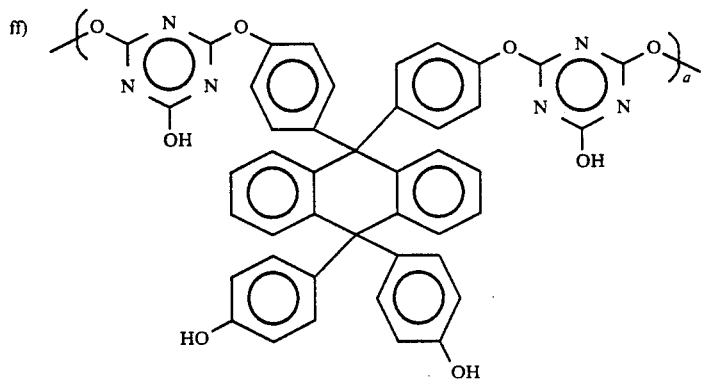
gg) 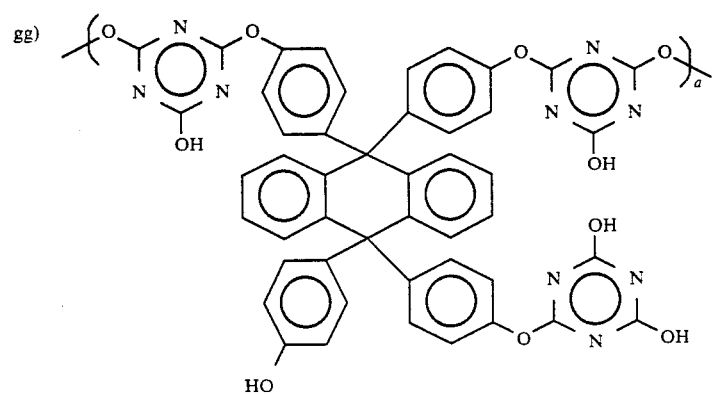
hh) 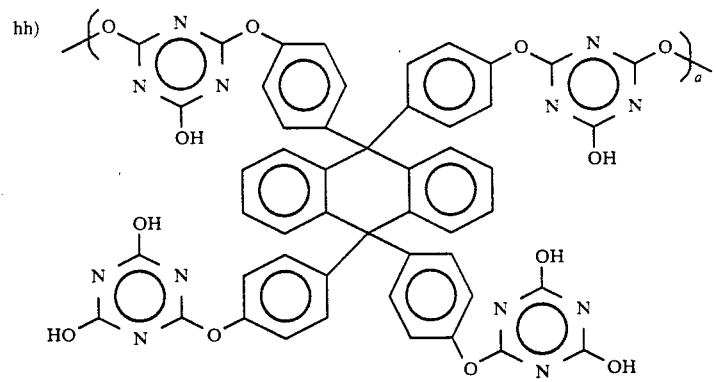
ii) 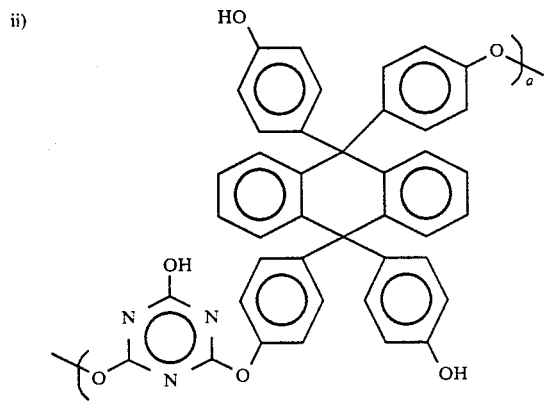

jj) 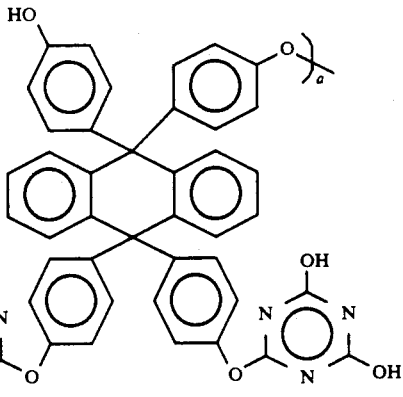

kk) 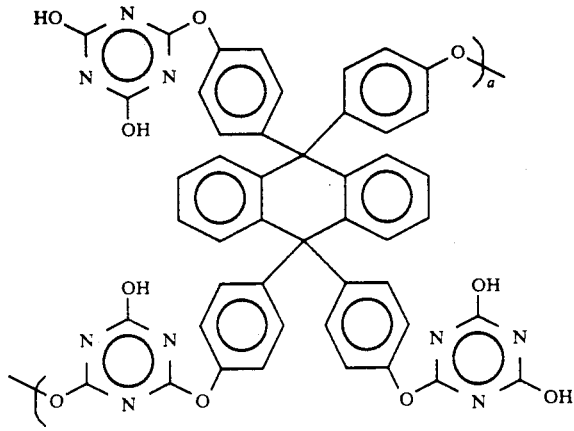

wherein the above structures, the integer a varies from 1 to 3000.

The corresponding names (i.e., nomenclature) for each of the above structures (i.e., formulas) are listed below in Table I.

TABLE I

Nomenclature - Structure Correlation For Product Description (a) through (kk)

a) mono(phenolphthalein ether)-di-hydroxy-triazine;
b) [o-(Phenolphthalein)-o'-(phenolphthalein)-]-diether-hydroxyl-s-triazine;
c) phenolphthalein-di-(di-hydroxy-s-triazine)ether;
d) poly[phenolphthalein-co-(hydroxyl)s-triazine]ether;
e) poly[star(phenolphthalein-co-s-triazine)ether];
f) mono(phenolphthalide ether-di-hydroxy-s-triazine);
g) [o-[phenolphthalide]-o'-(phenolphthalide)-[diether-hydroxyl-s-triazine;
h) phenolphthalide-di-(di-hydroxyl-s-triazine)-ether;
i) poly[phenolphthalide-co-(hydroxyl)-s-triazine]ether;
j) poly[star(phenolphthalide-co-s-triazine)-ether];
k) 9-(4-hydroxylphenyl)-9-(4-[di-hydroxyl-s-triazine]phenyl-ether)fluorene;
l) 4-(o-phenyl fluorene)-4-(o'-phenyl fluorene)diether hydroxyl-s-triazine;
m) di-9-[4(di-hydroxyl-s-triazine)phenyl ether]fluorene;
n) poly(9,9-phenylfluorene)-co-[(hydroxyl)-s-triazine]-ether;
o) poly[star(9,9-phenyl fluorene)-co-(s-triazine)-ether];
p) 3-hydroxy-6-(di-hydroxy-s-triazine)spiro(fluorene-9,9-xanthane);
q) 3,6-di(di-hydroxy-s-triazine)spiro(fluorene-9,9-xanthane);
r) poly[3,6-dihydroxylspiro(fluorene-9,9-xanthane)-co-(hydroxyl)-s-triazine]ether;
s) poly[star[tri(3,6-dihydroxyl(spiro[fluorene-9,9 xanthane-co-s-triazine]-ether];
t) 10,10-(4-hydroxyl phenyl)-dihydroxyl-s-triazine ether)-anthrone;
u) 10,10-[4-(o)-4'(o')-diether-s-triazine]anthrone;
v) 10,10-bis-(4-di-hydroxyl-s-triazine)ether-anthrone;
w) poly[10,10-(4-oxyphenyl)-4'(hydroxyl-s-triazine)anthrone];

TABLE I-continued

Nomenclature - Structure Correlation For Product Description (a) through (kk)

x) poly[star(tri-[10,10'-dihydroxyl phenyl-anthrone)-co-(s-triazine)-ether];
y) 9,10,10-tri(4-hydroxyl phenyl)-10-[4-(di-hydroxyl-s-triazine)phenyl ether]anthracene;
aa) 9,9[4-(o,o'-hydroxyl-s-triazine)-phenyl ether]-10,10-bis (4-hydroxylphenyl)-anthracene;
bb) 9,9-bis[4-(dihydroxyl-s-triazine)-phenyl ether]-10,10-bis-(4-hydroxyl phenyl)-anthracene;
cc) 9-(4-hydroxyl phenyl)-10-(4-hydroxyl phenyl)-9-[(4-dihydroxyl-s-triazine)phenyl ether]-10-[4-dihydroxyl-s-triazine)-phenyl ether]-anthracene;
dd) 9,9,-[(4-o,o',-hydroxyl-s-triazine-phenyl ether)-10,10-(4-o,o'-hydroxyl s-triazine)-phenyl ether]-anthracene;
ee) 9,9,10,10-tetrakis[(4-dihydroxyl-s-triazine)-phenyl ether]-anthracene;
ff) 9,9-[4-poly(oxyphenyl-co-4-(hydroxyl-s-triazine)-phenyl)-ether)]-10,10-bis(4-hydroxyl phenyl)-anthracene;
gg) 9,9-[4-poly(oxyphenyl-co-4-hydroxyl-s-triazine)phenyl ether)]-10-(4-hydroxyl phenyl)-10-(4-dihydroxyl-s-triazine-o-phenylether)anthracene;
hh) 9,9-[4-poly(oxyphenyl-co-4-hydroxyl-s-triazine)phenyl ether)]-10,10-bis(4-(dihydroxyl-s-triazine)phenyl ether)-anthracene;
ii) 9,10-[4-poly(oxyphenyl-co-4-hydroxyl-s-triazine)phenyl ether)]-9,10-bis-(4-hydroxyl phenyl)-anthracene;
jj) 9,10-[4-poly(oxyphenyl-co-4-hydroxyl-s-triazine)phenyl ether)]-9-(4-hydroxyl phenyl)-10-(4-dihydroxyl-s-triazine)-phenyl ether-anthracene; and
kk) 9,10-[4-poly(oxyphenyl-co-4-hydroxyl-s-triazine)phenyl ether]-9,10-bis(4-dihydroxyl-s-triazine-phenyl ether)-anthracene;

According to the present invention, a chemical method has been developed to solubilize reducing agent precursors in diesel fuel and to enhance their overall thermal stability. Upon thermal decomposition, the reducing agent precursors generate isocyanic acid, HNCO, depicted below in Equation 3 (Eq.3).

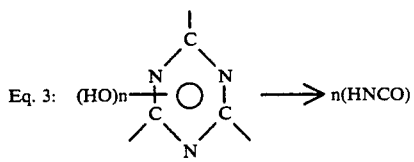

Eq. 3:

The reducing agent precursors are hydroxyl-s-triazines containing at least one hydroxyl function. The method of dissolution in diesel fuel and enhancing thermal stability of the molecule consists of a process entailing:
a) reacting an hydroxyl-s-triazine containing at least hydroxyl group (VII); a halo-s-triazine containing a functionality which may chemically converted insitu into a hydroxyl group (IX); and an alkaline salt of materials depicted in structures (a) through (kk); and
b) isolating said separating reaction product from impurities generated therefrom said process.

Chemical s-triazines amenable to this process may be selected from structures VII, VIII, and IX shown below.

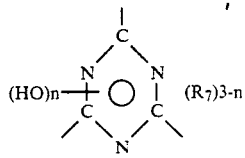

(VII)

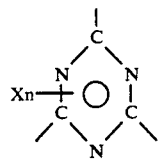

(VIII)

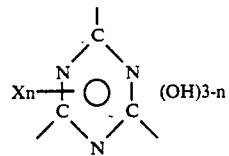

(IX)

In all cases (i.e., VII–IX), the integer n may vary from 1 to 3; $R_7$ is any inert non-reactive substituent. 'Non-reactive' shall mean non-reactive or inert to both the number of hydroxyl groups and to the chemical process. It may be selected from the group consisting of C1 to C10 hydrocarbons that may be alkyl, aryl, linear or branched or saturated or unsaturated. The letter X is any of the Group VIIa elements, although for economical reasons, it is especially desirable to limit (X) to chlorine.

For illustrative purposes only, phenolphthalein is shown below in Equation 4 (Eq. 4) reacting with trichloro-s-triazine. It is further emphasized that although the stoichiometry and reaction conditions and parameter have been adjusted to minimize oligomeric product formation. The products (i.e., a, b, c, d and e) of such reaction are provided below.

Eq. 4:

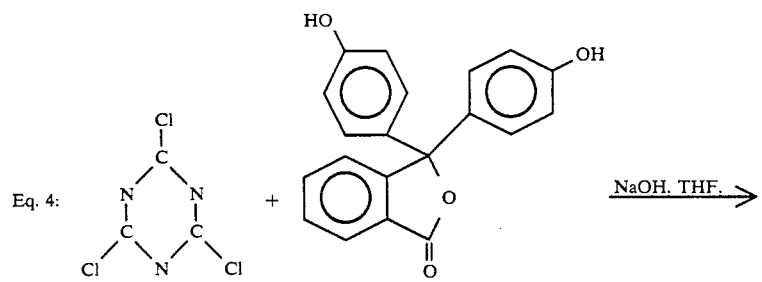

NaOH, THF, a)

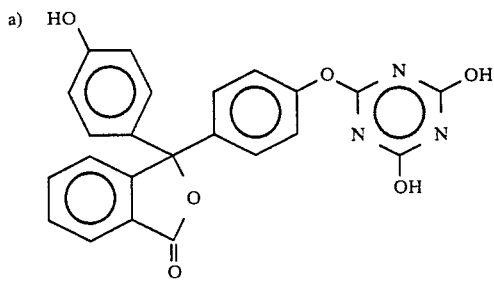

-continued
b) 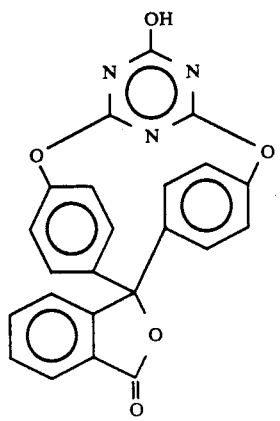
c) 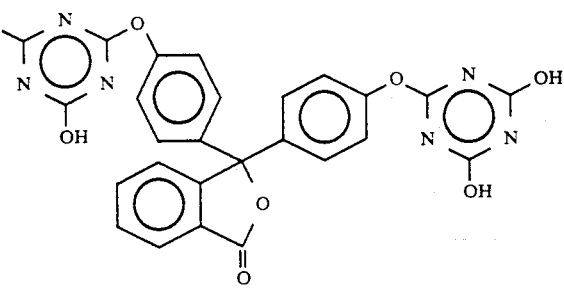
d) 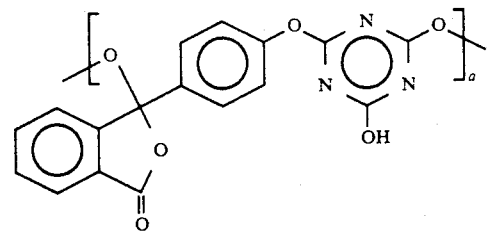
e) 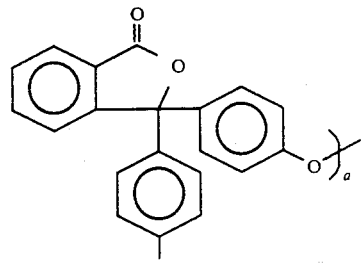

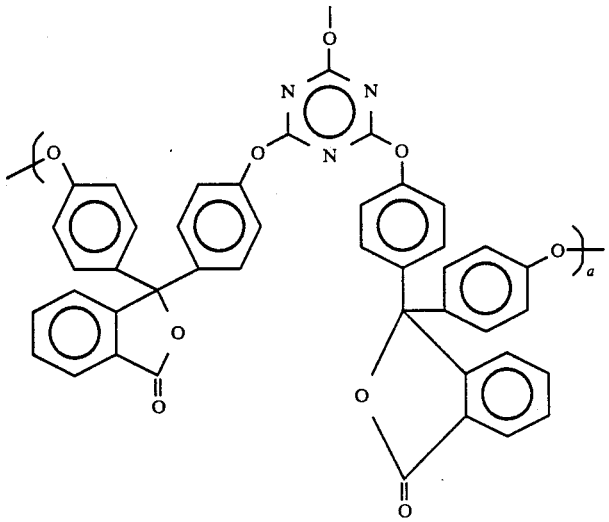

wherein the above structures, the integer a varies from 1 to 3000.

In order to further illustrate the present invention and its advantages, the following examples are provided.

EXAMPLE 1

Preparation of 3,3-bis(4'-hydroxylphenyl phenolphthalein

A three neck 1000 ml round bottom flask containing 150 parts phthalic anhydride, 400 parts phenol, and approximately 1 part anhydrous $ZnCl_2$ with 0.5 parts $SOCl_2$ is heated to 85° C. using a mechanical stirrer under a blanket of nitrogen for 6 hours. The mixture was subsequently steam distilled to remove unreacted phenol, phthalic anhydride and phthalic acid. The reaction mixture was subsequently dissolved in diethyl ether, filtered to remove residual phthalic anhydride, phthalic acid, and $ZmCl_2$, and isolated as a yellowish solid. Recrystallization was performed in n-hexane yielding a white crystal. $M_p$ 271° C.

EXAMPLE 2

Preparation of 3,3-bis (2'-methyl-4'hydroxyl phenyl phenolphthalein

Ortho-methyl phenol should be substituted for the phenol of Example 1 in this Example and the procedure of Example 1 should be followed in this Example to obtain the product herein.

EXAMPLE 3

Preparation of 3,3-bis (2'n-nonyl-4'hydroxyl phenyl)-phenolphthalein

Ortho-n-nonyl phenol should be substituted for the phenol of Example 1 in this Example and the procedure of Example 1 should be followed in this Example to obtain the product herein.

EXAMPLE 4

Preparation of 3-(2'-methyl-4'hydroxylphenyl -3-(2¹-n-nonyl-4'hydroxylphenyl-phenol phthalein A 1:1 mole ratio of ortho-methyl phenol and ortho-n-nonyl phenol should be substituted for the phenol of Example 1 in this Example and the procedure of Example 1 should be followed in this Exmple to obtain the product herein.

EXAMPLE 5

Preparation of 3-(4'hydroxyl phenyl)-3(2',6'di-t-butyl-4'hydroxyl)phenyl phenolphthalein A 1:1 mole ratio of 2,6-di-t-butyl-phenol and phenol should be substituted for the phenol of Example 1 in this Example and the procedure of Example 1 should be followed in this Example to obtain the product herein.

EXAMPLE 6

Preparation of 3,3-bis (4,4' hydroxyl phenyl-3,4,5,6 tetraphenyl)phenolphthalein 3,4,5,6 - tetraphenyl phthalic anhydride should be substituted for the phenol of Example 1 in this Example and the procedure of Example 1 should be follwed in this Example to obtain the product herein.

EXAMPLE 7

Preparation of N-phenyl-3,3-bis (4'hydroxyl-phenyl) phthalimidine

A 3-neck 1000 ml round bottom flask containing a magnetic stirrer, reflux condenser, and a nitrogen gas ingress tube is charged with 100 parts aniline hydrogen chloride and 100 parts phenolphthalein and 600 parts aniline and heated to reflux for 4 hours. The reaction mixture thereafter is distilled to remove unreacted aniline. The reaction mixture is added to anhydrous ethanol, filtered to remove unreacted aniline hydrogen chloride, followed by the addition of diethyl ether to remove unreacted phenolphthalein. Removal of solvents gives a yellowish brown solid isolated. It is recrystallized in ethanol giving a white crystal, mp=275° C.

EXAMPLE 8

Preparation of 9,9-bis (4-hydroxylphenol)-fluorene

A 500 ml 3-neck round bottom flask containing a gas ingress tube, magnetic stirrer, and a thermometer is charged with 3 parts phenol and heated until molten and 0.35 parts fluorenone added followed by 1.5 ml 3-mercapto-propionic acid as a cocatalyst. Anhydrous hydrogen chloride, is bubbled in at a rate of 2.5 l/min for 15 minutes and thereafter the mixture stirred for 1 hour. The mixture was subsequently purified by steam distillation to remove unreacted phenol, hydrogen chloride, and co-catalyst and the remaining mixture dissolved in 3M NaOH solution, filtered to remove unreacted fluorene, and acidified to yield a white precipitate which has a Mp of 224° C.

EXAMPLE 9

Preparation of 9,9-bis (2-methyl-4-hydroxyl phenyl) fluorene

Ortho methyl phenol should be substituted for the phenol of Example 8 in this Example and the procedure of Example 8 should be followed in this Example to obtain the product herein.

EXAMPLE 10

Preparation of 9,9-bis (2-n-nonyl-hydroxyl phenyl) fluorenone

Ortho-n-nonyl-phenol should be substituted for the phenol of Example 8 in this Example and the procedure of Example 8 should be followed in this Example to obtain the product herein.

EXAMPLE 11

Preparation of 3,6-di-hydroxyl spiro-[fluorene-9,9-xanthane]

Fluorenone (100 g) and resorcinol (200 g) were fused together at 180°-200° C., while dry hydrogen chloride was passed through the melt for 5 h. The reddish-brown product was poured out and cooled and then thoroughly washed with water to remove resorcinol. The bisphenol was recrystallized four times from toluene, and a glassy, yellowish crystal form which melted at 264° C.

EXAMPLE 12

Preparation of 10,10 bis-(4-hydroxyl phenyl) anthrone

Anthraquinone (60 g) phenol (150 g) and 3-mercapto-propionic acid (8 g) were placed in a round-bottom flask. The mixture was heated at 65° C., and then dry hydrogen chloride was bubbled in for about 24 h. The phenol, hydrogen chloride, and cocatalyst were removed by steam distillation. This product was recrystallized from methanol as a slightly yellowish granular mass: MP 320°-322° C.

EXAMPLE 13

Preparation of 10,10-bis (2-n-nonyl-4-hydroxyl phenyl) anthrone

Ortho-n-nonyl-phenol should be substituted for the phenol of Example 12 in this Example and the procedure of Example 12 should be follwed in this Exampke to obtain the product herein.

EXAMPLE 14

Preparation of 10-(4-hydroxyl phenyl)-10-(2-n-nonyl-4-hydroxyl phenyl) - anthrone A 1:1 weight ratio of phenol and a 2-n-nonyl-phenol should be substituted for the phenol of Example 12 in this Example and the procedure of Example 12 should be followed in this Example to obtain the product herein.

EXAMPLE 15

Preparation of 9,9,10,10-Tetrakis (4-hydroxyphenyl)anthracene

A mixture of 7.6 g 10,10-bis (p-hydroxyphenyl) anthrone, 10 ml alcohol, and 100 ml 10% sodium hydroxide solution was refluxed and 30 ml dimethyl sulfate was added gradually. It was heated for 1 h and the crystalline precipitate was recrystallized from acetic acid to give a white product. MP=208°-209° C.

EXAMPLE 16

Preparation of 9,9-bis(4-hydroxyl-phenyl)-10,10-(2-n-nonyl(4-hydroxylphenyl)anthracene Ortho-n-nonylphenol should be substituted for the phenol of Example 15 in this Example and the procedure of Example 12 should be followed in this Example to obtain the product herein.

EXAMPLE 17

Preparation of 9,9,10,10-tetrakis (2-nonyl-4-hydroxyl phenyl)anthracene)

The reaction product from Example 13 and 2-nonylphenol should be substituted for the phenol of Example 15 in this Example and the procedures of Example 12 should be followed in this Example to obtain the product herein.

EXAMPLE 18

Reaction of 3,3-bis (4'hydroxyl phenyl) phenolphthalein and trichloro-s-triazine In a 1000 ml 3-neck round bottom glass flask, 100 parts of 3,3-bis (4'-hydroxyl phenyl) phenolphthalein, the reaction product from Example 1, is dissolved in 300 ml tetrahydrofuran containing 6 parts sodium hydroxide. A co-solvent, n-hexane, 50 mls, is added to the reaction mixture followed by the addition of 7 parts water. While vigorously stirring at ambient temperature, 27 parts of trichloro-s-triazine dissolved in 150 ml THF is added dropwise using an addition funnel. The mixture is subsequently stirred at ambient temperature for 1 hour, then heated to reflux temperature for 3 hours. The mixture is cooled and filtered to remove NaCl. The solvent is distilled off at atmospheric pressure leaving a brown solid. The absence of C-Cl infrared absorbance at 628 cm$^{-1}$ and the appearance of an ether infrared absorbance at 1390 cm$^{-1}$ is evidence of a successful reaction.

EXAMPLE 19

Reaction of 3,3-bis (2'-methyl-4' hydroxyl phenyl) with tri-chloro-s-triazine phenolphthalein The reaction product from Example 2 should be substituted for the 3,3-bis(4'hydroxyl phenyl) phenolphthalein of Example 18, in this Example and the procedure of Example 18 should be followed in this Example to obtain the reaction product herein.

EXAMPLE 20

Reaction of 3,3-bis (2'n-nonyl-4'hydroxyl-phenyl) phenolphthalein with tri-chloro-s-triazine The reaction product from Example 3 should be substituted for the 3,3-bis (4'hydroxyl phenyl) phenolphthalein of Example 18 in this Example and the proce-

EXAMPLE 21

Reaction of 3-(2'-methyl)-4'hydroxylphenyl)-3-2'-n-nonyl-4'-hydroxylphenyl)phenolphthalein with trichloro-s-triazine The reaction product from Example 5 should be substituted for the 3,3-bis (4' hydroxyl phenyl) phenolphthalein of Example 18 in this Example and the procedure of Example 18 should be followed in this Example to obtain the reaction product herein.

EXAMPLE 22

Reaction of 3-(4'hydroxyl phenyl)-3'(2',6'-di-t-butyl-4-hydroxyl)phenyl phenolphthalein with tri-chloro-s-triazine The reaction product from Example 5 should be substituted for the 3,3-bis(4' hydroxyl phenyl) phenolphthalein of Example 18 in this Example and the procedure of Example 18 should be followed in this Example to obtain the reaction product herein.

EXAMPLE 23

Reaction of 3,3-bis(4'4'-hydroxyl phenyl-3,4,5,6-tetraphenyl)phenolphthalein with tri-chloro-s-triazine The reaction product from Example 6 should be substituted for the 3,3-bis(4'hydroxylphenyl) phenolphthalein of Example 18 in this Example and the procedure of Example 18 should be followed in this Example to obtain the reaction product herein.

EXAMPLE 24

Reaction of N-phenyl-3,3-bis (4'-hydroxyl-phenyl) phthalimidine

The reaction product from Example 7 should be substituted for the 3,3-bis (4'hydroxyl phenyl) phenolphthalein of Example 18 in this Example and the procedure of Example 18 should be followed in this Example to obtain the reaction product herein.

EXAMPLE 25

Reaction of 9,9 bis (2-methyl-4-hydroxyl phenyl) fluorene with trichloro-s-triazine The reaction product from Example 8 should be substituted for the 3,3-bis (4' hydroxyl phenyl) phenolphthalein of Example 18 in this Example and the procedure of Example 18 should be followed in this Example to obtain the reaction product herein.

EXAMPLE 26

Reaction of 9,9 bis(2-methyl-4-hydroxyl phenyl) fluorene with tri-chloro-s-triazine The reaction product from Example 9 should be substituted for the 3,3-bis (4'hydroxyl phenyl) phenolphthalein of Example 18 in this Example and the procedure of Example 18 should be followed in this Example to obtain the reaction product herein.

EXAMPLE 27

Reaction of 9,9-bis(2-n-nonyl-4-hydroxyl-phenyl) fluorene with tri-chloro-s-triazine The reaction product from Example 10 should be substituted for the 3,3-bis (4'hydroxyl phenyl) phenolphthalein of Example 18 in this Example and the procedure of Example 18 should be followed in this Example to obtain the reaction product herein.

EXAMPLE 28

Reaction of 3,6-di-hydroxyl spiro-[fluorene-9,9'xanthane] with tri-chloro-s-triazine The reaction product from Example 11 should be substituted for the 3,3-bis (4'hydroxyl phenyl) phenolphthalein of Example 18 in this Example and the procedure of Example 18 should be followed in this Example to obtain the reaction product herein.

EXAMPLE 29

Reaction of 10,10,bis-(4-hydroxyl phenyl) anthrone with tri-chloro-s-triazine

The reaction product from Example 12 should be substituted for the 3,3-bis (4'hydroxyl phenyl) phenolphthalein in Example 18 in this Example and the procedure of Example 18 should be followed in this Example to obtain the reaction product herein.

EXAMPLE 30

Reaction of 10,10-bis (2-n-nonyl-4-hydroxylphenyl) anthrone with tri-chloro-s-triazine The reaction product from Example 13 should be substituted for the 3,3-bis (4'hydroxyl phenyl) phenolphthalein in Example 18 in this Example and the procedure of Example 18 should be followed in this Example to obtain the reaction product herein.

EXAMPLE 31

Reaction of 10-(4-hydroxyl phenyl)-10-2'-nonyl-4-hydroxyl phenyl) anthrone with tri-chloro-s-triazine The reaction product from Example 14 should be substituted for the 3,3-bis (4'hydroxyl phenyl) phenolphthalein in Example 18 in this Example and the procedure of Example 18 should be followed in this Example to obtain the reaction product herein.

EXAMPLE 32

Reaction of 9,9,10 tetrakis (4-hydroxylphenyl) anthracene with tri-chloro-s-triazine The reaction product from Example 15 should be substituted for the 3,3-bis (4'hydroxyl phenyl) phenolphthalein in Example 18 in this Example and the procedure of Example 18 should be followed in this Example to obtain the reaction product herein.

EXAMPLE 33

Reaction of 9,9-bis-(4-hydroxylphenyl)-10,10-bis (2-n-nonyl-4-hydroxyl phenyl) anthracene with tri-chloro-s-triazine The reaction product from Example 34 should be substituted for the 3,3-bis (4'hydroxyl phenyl) phenolphthalein in Example 18 in this Example and the procedure of Example 18 should be followed in this Example to obtain the reaction product herein.

EXAMPLE 34

Reaction of 9,9,10,10-tetrakis (2-nonyl-4-hydroxyl phenyl) anthracene with tri-chloro-s-triazine The reaction product from Example 16 should be substituted for the 3,3-bis (4'hydroxyl phenyl) phenolphthalein in Example 18, in this Example and the procedure of Example 18 should be followed in this Example to obtain the reaction product herein.

TESTING AND EVALUATION

The materials synthesized according to the present invention and illustrated in the above Examples, were structurally and physically evaluated. The key structural property of interest was the detection of hydroxyl-s-triazines. This evaluation was performed using Fourier Transform Infrared spectroscopy (FTIR). Results of FTIR studies are summarized in Table II. High pressure liquid chromatography was performed to determine the number of materials present within each experimental sample. Results of this investigation and experimental separation parameters are summarized in Table III.

Physical testing was concerned with the solubility of samples in diesel fuel and thermal stability of the neat sample. Results of solubility studies are summarized in Table IV. Thermal stability studies were performed using Thermal Gravimetric Analysis (TGA) and results are provided in Table V.

All FTIR evaluations for experimental samples were obtained using films produced using THF as the solvent and NaCl discs. FTIR analysis for cyanuric acid was performed by suspending in Nyjol mineral oil. The results for selected samples are provided below in Table II.

TABLE II

Detection Of Encapsulated Hydroxyl-s-Triazine Using FTIR

| Sample | Phenolic OH Stretch (cm-1) | Phenolic OH Deformation (cm-1) | Cyanuric Acid OH Stretch (cm-1) | Cyanuric Acid OH Deformation (cm-1) |
|---|---|---|---|---|
| Cyanuric Acid | — | — | 3203 | 1390 |
| Example 18 | 3419, 3065, 3022 | 1216 | 3203 | 1380 |
| Example 23 | 3462, 3081, 3016 | 1233 | 3204 | 1380 |
| Example 26 | 3465, 3087, 3050 | 1237 | 3203 | 1381 |
| Example 29 | 3478, 3030, 3004 | 1222 | 3200 | 1382 |
| Example 32 | 3472, 3061, 3005 | 1226 | 3215 | 1380 |
| Example 34 | 3479, 3043, 3006 | 1239 | 3216 | 1383 |

TABLE III

Summary Of Peak Detection Of Experimental Samples Using HPLC
The column used for the analysis was non-polar (C18; HS-3 C1) reverse phase using a sample concentration of 16.0 mg/10 mls THF. The injection volume was routinely 20 microliters and a detection wavelength was 250 nm was used for all samples.

| Sample Mixture | Components Detected |
|---|---|
| Example 18 | 9 |
| Example 23 | 7 |
| Example 26 | 6 |
| Example 29 | 6 |
| Example 32 | 3 |
| Example 34 | 3 |

TABLE IV

Maximum Solubility Of Encapsulated Hydroxyl-s-Triazines In Poly[1-Hydroxyl-(2,6-Phenylene Methylene)] Derivatives In Diesel Fuel

| Sample | Solute Concentration at Turbidity Point (wt %) |
|---|---|
| Example 18 | 1.5 |
| Example 23 | 10 |
| Example 26 | >0.5 |
| Example 29 | 20 |
| Example 32 | 14 |
| Example 34 | 50.0 |

TABLE V

Thermal Decomposition Of Modified cyanmeric acids Encapsulated Using A Heating Rate Of 200 Deg C./min Under Nitrogen

| Sample | 50 wt % Decomposition Temp. (deg C.) | 90 wt. % Loss Decomposition Temp. (deg. C.) |
|---|---|---|
| Example 18 | 490 | 660 |
| Example 21 | 565 | 785 |
| Example 23 | 665 | <920 |
| Example 26 | 570 | <920 |
| Example 29 | 610 | 790 |
| Example 32 | 550 | 835 |
| Example 34 | 600 | 850 |

It is readily apparent from structural and physical characterization that a new composition of matter has been invented, namely, encapsulated hydroxyl-s-triazines that exhibit unique and heretofore novel properties.

We claim:

1. A compositon of matter prepared by the process comprising reacting phenolphthaleins represented by the formula

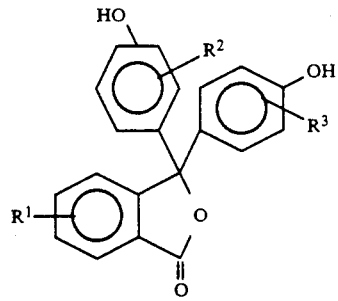

where $R^1$, $R^2$, and $R^3$ are each a ($C_1$–$C_{10}$) linear, cyclic, branched or aromatic hydrocarbon,
with cyanuric chloride, thereby preparing said composition of matter which comprises:
 a) mono(phenolphthalein ether)-di-hydroxy-triazine;
 b) [o-(Phenolphthalein)-o'-(phenolphthalein)-]-diether-hydroxyl-s-triazine;

c) phenolphthalein-di-(di-hydroxy-s-triazine)ether;

d) poly[phenolphthalein-co-(hydroxyl)s-triazine]ether; and e) poly[star(phenolphthalein-co-s-triazine)ether].

2. A composition of matter prepared by the process comprising reacting 9,9-bis (4-hydroxylphenyl) fluorenes represented by the formula

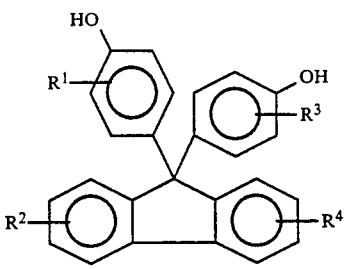

where $R^1$ $R^2$, $R^3$, and $R^4$ are each a ($C_1$–$C_{10}$) linear, cyclic, branched or aromatic hydrocarbon, with cyanuric chloride, thereby preparing said composition of matter which comprises:

k) 9-(4-hydroxylphenyl)-9-(4-[di-hydroxyl-s-triazine]phenylether)fluorene;

l) 4-(o-phenyl fluorene)-4-(o'-phenyl fluorene) diether hydroxyl-s-triazine;

m) di-9-[4(di-hydroxyl-s-triazine) phenyl ether] fluorene;

n) poly(9,9-phenylfluorene)-co-[(hydroxyl)-s-triazine]-ether; and o) poly[star (9,9-phenyl fluorene)-co-(s-triazine)-ether].

* * * * *